United States Patent [19]

Nowacki et al.

[11] Patent Number: 4,621,634
[45] Date of Patent: Nov. 11, 1986

[54] ANESTHESIA TUBING CONNECTIONS

[75] Inventors: Christopher Nowacki, Arlington Heights; Alfred G. Brisson, Schaumburg, both of Ill.

[73] Assignee: Trutek Research, Inc., Arlington Hts., Ill.

[21] Appl. No.: 574,341

[22] Filed: Jan. 27, 1984

[51] Int. Cl.⁴ ............................................. A61M 16/00
[52] U.S. Cl. ............................... 128/204.18; 128/911; 128/912; 604/905; 604/283; 138/108; 138/109; 138/111; 285/131; 285/317; 403/377
[58] Field of Search ............. 128/911, 204.18, 207.14, 128/207.15, 207.17, 205.25, 201.11; 604/905, 293; 285/131, 133 R, 317; 138/108, 109, 110, 111, 112, 113, 114, 121; 403/377

[56] References Cited

U.S. PATENT DOCUMENTS

| 593,190 | 11/1897 | Bernhardt | 285/317 |
| 1,096,690 | 5/1914 | Derbyshire | 285/317 |
| 2,831,487 | 4/1958 | Tafilaw | 128/DIG. 26 |
| 3,394,954 | 1/1968 | Sarns | 604/905 |
| 3,789,129 | 1/1974 | Ditscheid | 138/113 |
| 4,007,737 | 2/1977 | Paluch | 128/911 |
| 4,019,508 | 4/1977 | Der Estephanian et al. | 128/910 |
| 4,320,754 | 3/1982 | Watson et al. | 128/911 |
| 4,440,154 | 4/1984 | Bellows | 138/112 |
| 4,463,755 | 8/1984 | Suzuki | 128/911 |
| 4,468,225 | 8/1984 | Tcheraz | 604/905 |
| 4,521,038 | 6/1985 | Cerny | 128/911 |

FOREIGN PATENT DOCUMENTS

| 0054714 | 6/1982 | European Pat. Off. | 128/207.15 |
| 2013463 | 4/1970 | France | 128/911 |
| 2025239 | 1/1980 | United Kingdom | 128/911 |

Primary Examiner—Henry J. Recla
Attorney, Agent, or Firm—Trexler, Bushnell & Wolters, Ltd.

[57] ABSTRACT

Improved connectors are disclosed for a Bain anesthesiology circuit. At the end remote from the patient, positive connections are made to the anesthesiology gas supply tube. The construction of the fitting for the exhaust is such as to apply a crank action, facilitating tight insertion of the fitting into an exhaust connector. At the patient end a positive locking connection is made to the endotracheal tube or the like, and a secure connection permitting a certain degree of turning without twisting of the inner tube is provided.

10 Claims, 8 Drawing Figures

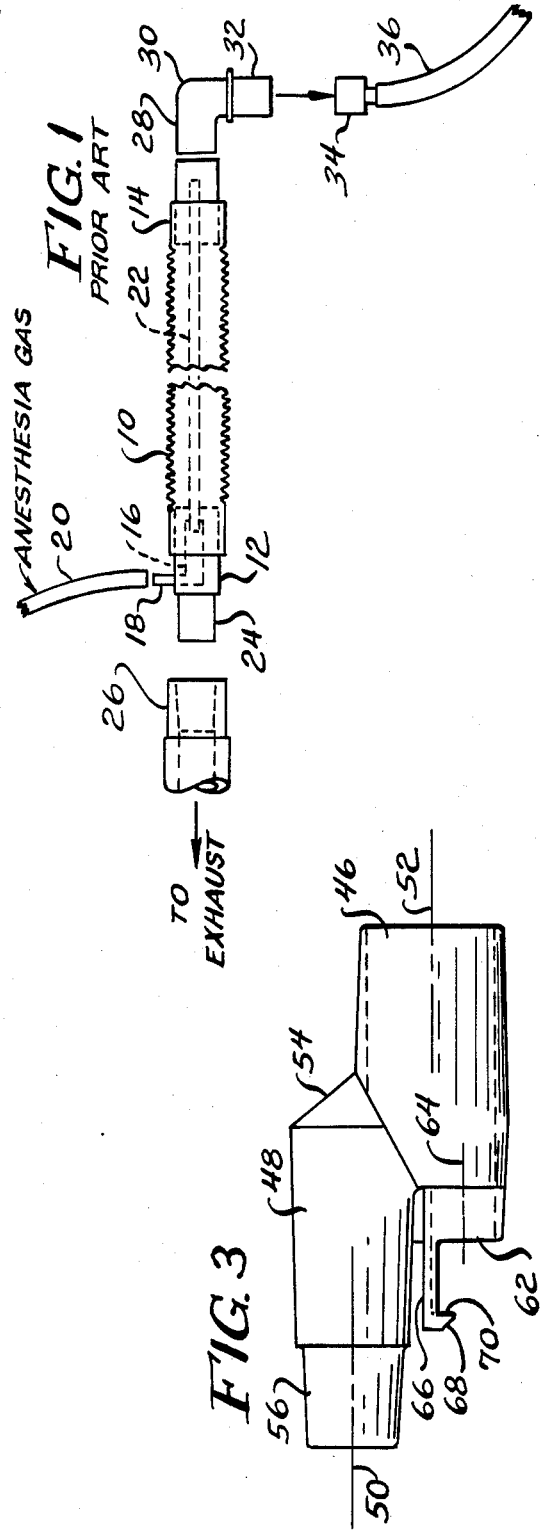
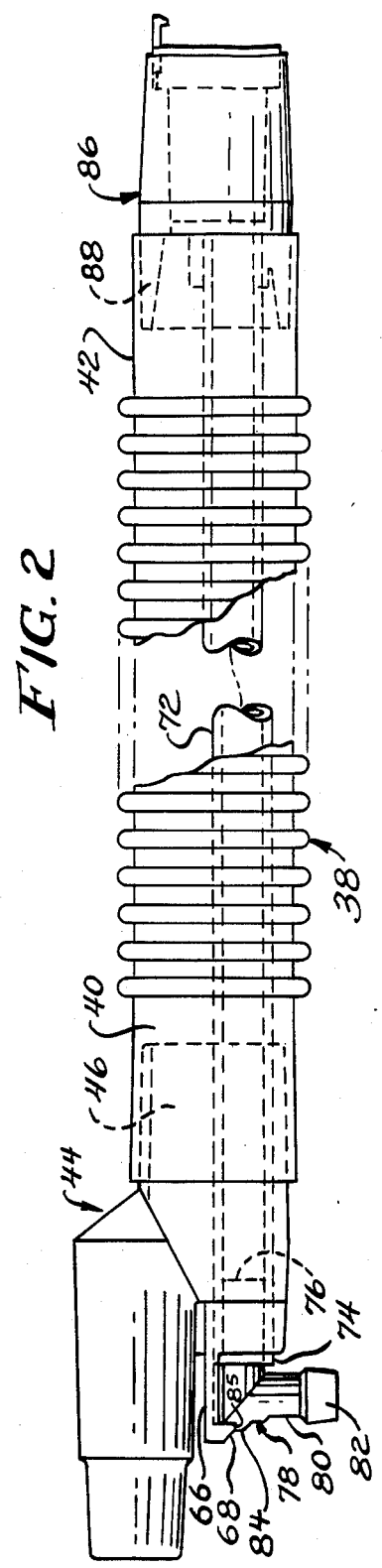

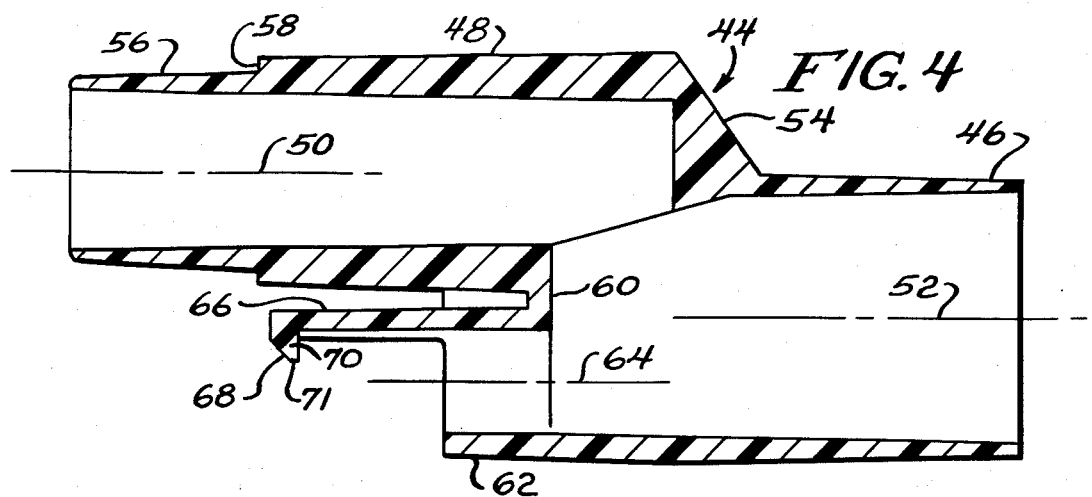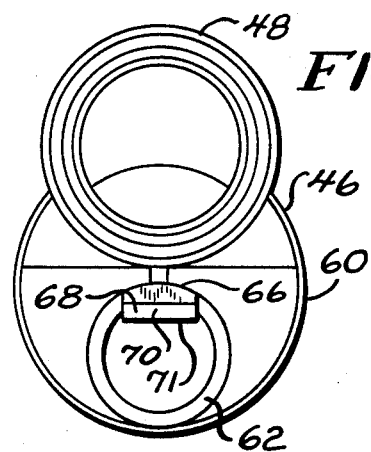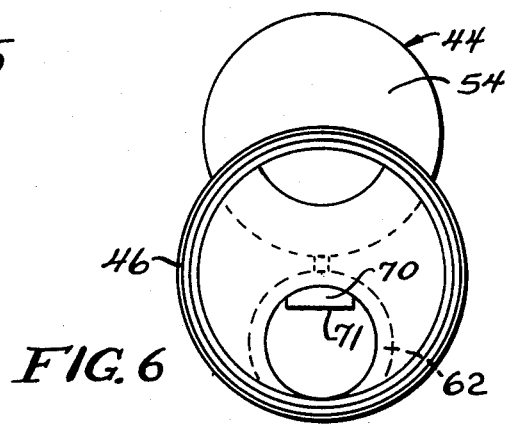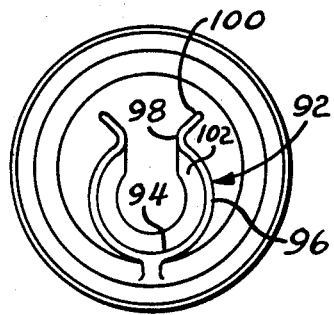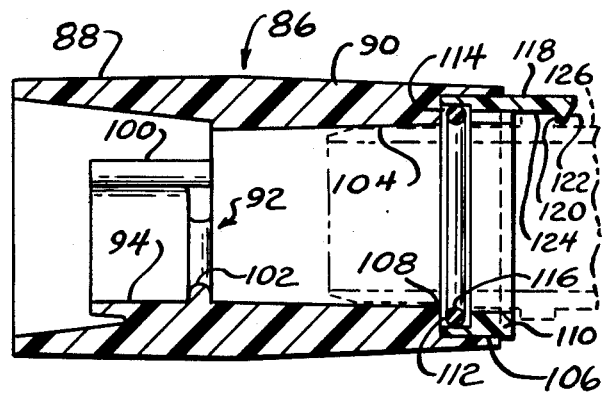

ANESTHESIA TUBING CONNECTIONS

RELATED APPLICATIONS

The present application is related to our prior copending application Ser. No. 540,324, filed Oct. 11, 1983 for "Anesthesiology Connector", assigned to the same assignee as the present application, namely Trutek Research, Inc., of Arlington Heights, Ill.

BACKGROUND OF THE INVENTION

Anesthesia can be delivered to a patient either intermittently, with rather complicated valving, as a patient alternately inhales and exhales, or it may be administered continuously. One commercial circuit for the continuous application of anesthesia is sometimes known as a coaxial circuit. In accordance with this known circuit there is an exterior corrugated, flexible tube connected at the patient end to an endotracheal tube or a mask, and connected at the other end to an exhaust, preferably a scavenger system. An inner flexible tubing, generally non-corrugated, terminates at the patient end within the outer tube, generally near the end thereof, and at the opposite end exits laterally of the outer tube. Anesthesia gas is provided to the lateral end. The gas so supplied generally comprises an anesthetic gas mixed with air or oxygen. As the patient inhales he receives gas from the inner tube. When he exhales he dispells used anesthesiology gas into the exhaust system, and a certain amount of fresh gas also is bypassed into the exhaust system.

In the known coaxial circuit, as in most anesthetic circuits in use today, connections usually comprise press fits of plastic parts. Such connections usually are satisfactory, but they can come apart with considerable danger to the patient, and some danger to the surgical team. Furthermore, such fittings are often rather hard to assemble properly.

OBJECTS AND SUMMARY OF THE PRESENT INVENTION

It is an object of the present invention to provide improved connections for anesthesia tubing.

It is a further object of the present invention to provide positive locking separable connectors for a coaxial circuit anesthesic tubing accompanied by structure for more simply and tightly connecting a tapered fit for the exhaust tubing.

In accordance with the present invention an improved coaxial circuit is provided in which a snap-over positive locking connection is provided at the patient end. A positive snap-over fitting for the anesthesia gas also is provided at the inlet end. This latter fitting is radially offset from the exhaust fitting, thereby providing a crank effect facilitating assembly of the tapered exhaust fitting, thereby assuring a tighter connection.

THE DRAWINGS

The present invention will best be understood with reference to the following detailed description when taken in connection with the accompanying drawings wherein:

FIG. 1 is a side view of the prior art Bain circuit;

FIG. 2 is a side view of the improved circuit of the present invention;

FIG. 3 is a side view of the inlet end fitting;

FIG. 4 is a longitudinal sectional view through the fitting of FIG. 3;

FIG. 5 is an end view taken from the left end of FIG. 4;

FIG. 6 is an end view taken from the right end of FIG. 4;

FIG. 7 is an axial sectional view through the patient end fitting; and

FIG. 8 is an end view of the fitting of FIG. 7 taken from the left end thereof.

DETAILED DISCLOSURE OF THE ILLUSTRATED EMBODIMENT

Turning now to FIG. 1 there is shown an exemplification of the prior art Bain circuit including an external corrugated flexible plastic tubing 10 having a tapered fitting 12 at the left or remote end, and a tapered fitting 14 at the patient end. The tapered fitting 12 is provided with a smaller elbow fitting 16 exiting radially at 18 through the side of the fitting 12 for receipt of a flexible tube 20 carrying anesthetic gas. This may be straight anesthetic gas, or it may be a mixture of anesthetic gas with air or oxygen.

A small diameter flexible tubing 22 is provided within the corrugated tubing 10 and its left end is received in the end of the elbow 16. The right end of the flexible tubing 22 is secured within the tapered fitting 14, and both ends of the tubing preferably are fixedly secured by means of solvent welding.

The fitting 12 is provided at the left end with a tapered male cylinder 24 to be received in a tapered female fitting 26 leading to a scavenging system which may include blowers, etc., for disposing of used anesthetic gas and a certain amount of fresh anesthetic gas. The fitting 14 includes an internal tapered female receptacle for receiving the tapered male end 28 of an elbow 30 having a tapered female end 32 for receipt of the male connector 34 or an endotracheal tube 36. Alternatively, a mask may be used rather than the endotracheal tube.

Fresh anesthetic gas is provided through the tube 20 and the elbow 16 to the inner tubing 22, the gas passing through the elbow 30 to the endotracheal tube 36 as the patient inhales. When the patient exhales, used anesthetic gas and carbon dioxide, etc., from the patient's lungs pass out through the endotracheal tube, through the elbow 30, and through the corrugated tubing 10 to the fitting 12, and hence through the female fitting 26 to the exhaust system. During the time that the patient exhales anesthetic gas continues to exit from the tubing 22, and simply is exhausted along with the exhaled gas.

Turning now to the remaining figures, and particularly to FIGS. 2-6, there will be seen an improved coaxial circuit constructed in accordance with the present invention. This includes an outer corrugated tube 38 similar to the previously identified tube 10 and having left and right cylindrical ends 40 and 42 having the extremities thereof flared outwardly by association with accompanying male fittings. In particular, at the left end there is provided an offset fitting 44 having a tapering entering end portion 46 forming a tight fit within the cylindrical end 40 of the corrugated tubing 38 and flaring the same outwardly to form a retentive connection. Upwardly and to the left of the entering end portion 46 there is a tubular exhaust cylinder 48 having the interior thereof opening into the interior of the entering end portion 46. The axes of these two portions are radially offset. The axis 50 of the tubular exhaust cylinder 48 substantially coincides with an element of the entering end portion 46, while the axis 52 of the entering end portion lies outside of and below the lower limit of the tubular exhaust cylinder 48. A frusto-conical section 54 joins the tubular exhaust cylinder to the tapered entering end portion 46.

The left end of the tubular exhaust cylinder is provided with a tapered male friction fitting 56 joined to the major portion of the cylinder 48 at a step or shoulder 58. This portion interfits with the exhaust connection such as 26 in FIG. 1.

The tapering entering end portion 46 is provided with a transverse end wall 60 joined to the exterior of the tubular exhaust cylinder 48 and closing off the end portion of the tapering entering end portion that does not enter into the tubular exhaust cylinder 48, except for a smaller lower opening surrounded by a tubular female connector 62 having a slightly tapering inner bore. The axis 64 of this female connector is offset from the axis 52 in the opposite direction from the axis 50. A latch member 66 extends outwardly (to the left) from the upper portion of the female connector 62 and forms a portion of a cylinder in cross section. At the outer end of the extension 66 there is a transverse depending wall having a tapered outer edge 68, and forming a retaining hook 70 having a flat lower edge 71. All of the parts of the offset fitting 44 as now enumerated are integrally molded of a suitable resinous plastic material. An inner flexible plastic hose or tube 72 of relatively small diameter extends through the tubular fitting 62 and outwardly thereof as shown at 74. The slightly tapering right end 76 of a molded resinous plastic elbow 78 plugs into the end 74 of the hose or tubing 72 and extends within the tubular female connector 62, tightly gripping the tube between the tubular female connector and the tapering end 76 of the elbow and holding the end of the tube in clearly visible position. The elbow has a downwardly extending arm 80 with a tapered enlargement 82 thereon over which an anesthesic gas connector tubing, such as the tubing 20 in FIG. 1, is received. The end of the tubing extends past the enlargement 82, and due to its resiliency hugs the portion of the arm 80 above the enlargement 82, thereby holding fast on the arm 80. In addition, a hose clamp can be provided if desired. The left-most surface of the arm 80 is provided with an enlargement 84 having a flat upper surface 85. As will be apparent the flat lower edge 71 of hook 70 engages the flat upper surface 85 of the enlargement 84, thereby positively retaining the right arm 76 of the elbow 78 in the female connector 62, thus aggressively locating the end 74 of the inner tube 72 therein, and securing the elbow against rotation about the end or arm 76. The arm or extension 66 can be manually flexed upwardly to release the elbow if it is desired to retract the same for any reason.

The offset of the tubular female connector 62 relative to the tubular exhaust cylinder allows the former to act somewhat as a crank for rotating the exhaust cylinder back and forth while inserting it into the female connector of the exhaust system. This materially facilitates assembly. Conversely, the offset of the tubular exhaust cylinder relative to the tapered connecting end portion 46 allows arcuate rocking of the latter while it is inserted into the end 40 of the corrugated tubing 38. Thus, the offset construction insures superior wedging connections as just noted. The hook 70 insures a superior connection of the elbow 78 with the inner tubing 72, and insures a superior connection of the latter within the tubular female connector 62.

At the right or patient end 42 of the corrugated tubing 38 there is provided a bevel ended tubular male connector 86, FIGS. 2, 7 and 8. At the left end there is a tapering male fitting 88 covering somewhat less than half of the length of the connector 86 and adapted to fit tightly within the end 42 of the corrugated tubing 38 and to deflect part of such end outwardly. The double ended connector 86 has a right end connecting portion 90 shown as straight on but which could be an elbow. This is for connection to an endotracheal tube or to a mask, and more will be said about this shortly.

The entire fitting 86 is molded of a suitable resinous plastic material, and an integral clip 92 is molded within the tapered connecting portion 88 and spaced inwardly from the end thereof. The clip is integral with the connector portion 88 along the bight 94 of the clip, and includes a pair of upwardly extending, nearly semi-circular arms 96 having a point of closest approach 98, and then flared outwardly at 100. The arms of the clip are each provided with an internal rib 102 joining together to form a continuous rib. The patient end of the inner tube 72 is pushed into this clip for secure retention. The left end of the inner tube 72 is secured first, and the tube is allowed to lie straight out before securement in the clip, whereby to avoid any initial twist in the tube that might cause kinking. The internal rib 102 forms a stop for the plastic tube 72, whereby a certain amount of turning of the tube within the clip is permitted, further avoiding any tendency of the inner tube to kink. Conversely, if the corrugated tubing 78 is twisted somewhat the inner tube 72 need not twist with it. Sometimes an inner corrugated tube may be used, and in this instance the rib will be received between adjacent corrugations.

The right end 90 of the connector 86 is similar in construction to the Anesthesiology Connector disclosed and claimed in our co-pending application Ser. No. 540,324, filed Oct. 11, 1983. In particular, there is an internal, tapered bore 104 having a recess 106 at the outer end thereof with a shoulder 108 at the inner edge of the recess. A ring 110 is cemented in the recess 106 and has an inner relieved portion 112 forming with the shoulder 108 a groove 114 in which an O ring 116 is disposed. The ring 110 extends slightly beyond the end of the fitting end 90 and is provided with an axially extending arm 118 having a hook 120 thereon with a tapered forward portion 122. The hook interlocks with a ring 124 on the connector 126 of an endotracheal tube or mask. Thus, secure connections are made at the patient end of the tubing 38, 72.

The O-ring 116 is important in that it permits the rise of joining cylindrical surfaces. If common tapered surfaces were used production tolerances could cause the endotrachael tube to reach a limit position in the base 104 at a position short of that necessary for the hook 120 lockingly to engage with the endotrachael tube. The O-ring further compensates for surface irregularities in the molded plastic parts which otherwise could cause improper sealing.

The most secure connections are made at the left or remote end of the tubing, since the tubing is most likely to be moved relative to the supply tube and the exhaust system, particularly when being brought into engagement with the patient.

Inexpensive and secure anesthesiology tubing connectors have been disclosed herein. They are more secure than those in the prior art due to interlocking construction, and also due to the crank nature of certain of the parts which facilitates a secure connection due to superior assembly of the parts. The specific example of the invention as herein shown and described is by way of example only. Various changes in structure will no doubt occur to those skilled in the art, and will be understood as forming a part of the present invention insofar as they fall within the spirt and scope of the appended claims.

The invention is claimed as follows:

1. Anesthesia apparatus including an outer flexible tube of predetermined diameter and having a patient end and a remote end, an inner flexible tube of lesser diameter disposed within said outer tube and extending substantially from end-to-end thereof, connection means secured to said patient end of said outer tube, said connection means having means for securing the corresponding end of said inner tube and further having means for mounting a patient anesthetic device such as an endotracheal tube, and remote connection means at the remote end of said outer tube, said remote connection means including a first tubular portion having a first end interfitting with said outer tube and a closed opposite end, a smaller inlet tubular portion within said first tubular portion and having an axis substantially parallel to and offset from the axis of said first tubular portion in a given direction, said smaller inlet tubular portion having a first and interfitting with said inner tube and an opposite end extending through said closed opposite end of said first tubular portion and adapted to interfit with a supply connector for anesthesia gas, and an exhaust tubular portion having a first end adapted to interfit with an exhaust system, said exhaust portion having an opposite end radially overlapping and being joined to and communicating internally with the interior of said first tubular portion and having an axis substantially parallel to and offset from the axis of said first tubular portion substantially opposite to said given direction, an offset portion sealingly joining said exhaust tubular portion to said first tubular portion and disposed in part beyond the circumference of said first tubular portion, said first tubular portion serving as a crank to said exhaust portion for rotating said remote connection means back and forth to interfit said remote connection means with said outer tube and with an exhaust system.

2. Apparatus as set forth in claim 1 wherein said inner tubing extends through said inlet tubular portion, and further including an inlet connector having a male portion received in said inner tubing within said inlet tubular portion.

3. Apparatus as set forth in claim 2 wherein said inlet connector comprises an elbow, an abutment on the corner of said elbow, and a retaining latch or said remote connection means engageable with said abutment.

4. Apparatus as set forth in claim 3 wherein said abutment comprises an enlargement on said elbow.

5. Apparatus as set forth in claim 2 wherein the patient end connection means comprises an internal integral clip receiving the corresponding end of said inner tube.

6. Apparatus as set forth in claim 5 and further including an inwardly projecting rib in said clip.

7. Apparatus as set forth in claim 1 wherein the patient end connection means comprises an internal integral clip receiving the corresponding end of said inner tube.

8. Apparatus as set forth in claim 7 and further including an inwardly projecting rib in said clip.

9. Apparatus as set forth in claim 1 wherein the patient end connection means comprises an internal integral clip receiving the corresponding end of said inner tube.

10. Apparatus as set forth in claim 9 and further including an inwardly projecting rib in said clip.

* * * * *